United States Patent
Ness (10) Patent No.: US 11,122,995 B2
(45) Date of Patent: Sep. 21, 2021

(54) PATIENT MEASUREMENT DEVICE AND RELATED METHODS

(71) Applicant: Trustees of Tufts College, Medford, MA (US)

(72) Inventor: Brandon Ness, Elk Point, SD (US)

(73) Assignee: TRUSTEES OF TUFTS COLLEGE, Boston, MA (US)

( * ) Notice: Subject to any disclaimer, the term of this patent is extended or adjusted under 35 U.S.C. 154(b) by 287 days.

(21) Appl. No.: 16/030,286

(22) Filed: Jul. 9, 2018

(65) Prior Publication Data

US 2019/0008418 A1 Jan. 10, 2019

Related U.S. Application Data

(60) Provisional application No. 62/529,878, filed on Jul. 7, 2017.

(51) Int. Cl.
*A61B 5/00* (2006.01)
*A61B 5/11* (2006.01)
*A61B 5/107* (2006.01)

(52) U.S. Cl.
CPC .......... *A61B 5/1121* (2013.01); *A61B 5/4528* (2013.01); *A61B 5/1071* (2013.01); *A61B 5/4595* (2013.01)

(58) Field of Classification Search
CPC .......... A61B 2560/0431; A61B 5/1072; A61B 5/1126; A61B 6/4452; A61B 5/1121; A61B 5/4528; A61B 5/4595; A61B 5/1071; F04D 3/00; G01B 11/02
USPC .......... 600/587, 595; 33/511, 512, 515, 832
See application file for complete search history.

(56) References Cited

U.S. PATENT DOCUMENTS

| | | | | | |
|---|---|---|---|---|---|
| 3,808,694 | A | * | 5/1974 | Hutchinson | G01G 23/37 33/512 |
| 3,955,285 | A | * | 5/1976 | Moeckl | A61B 5/1077 33/515 |
| 4,418,477 | A | * | 12/1983 | Montgomery | A41H 1/02 33/514.2 |

(Continued)

FOREIGN PATENT DOCUMENTS

DE 102010022375 A1 12/2011
DE 102014016468 A1 6/2016

OTHER PUBLICATIONS

Ankle Injury Management. "Guide for assessing ankle range of movement for the AIM trial." Nov. 15, 2010. Accessed online at https://web.archive.org/web/20170508144806/http://www.aimtrial.org/index.php?page=download&file_id=29.

(Continued)

*Primary Examiner* — May A Abouelela
(74) *Attorney, Agent, or Firm* — Quarles & Brady LLP (57) ABSTRACT

Disclosed herein are various patient measurement devices having an extendable elongate body and a deployable arm rotatably coupled to the elongate body. The elongate body has a first body comprising a lumen defined along a length of the first body and a second body extendably disposed within the lumen of the first body. The deployable arm is rotatably coupled to an end of the second body and is rotatably movable between a retracted position and a deployed position. Also disclosed are various methods of using the device to take various range-of-motion measurements, other physical capability measurements, and anthropometric measurements.

20 Claims, 8 Drawing Sheets

(56) References Cited

U.S. PATENT DOCUMENTS

| | | | | |
|---|---|---|---|---|
| 5,402,585 | A | 4/1995 | Lund | |
| 5,554,090 | A | 9/1996 | Jones | |
| 5,807,280 | A * | 9/1998 | Davis | A61B 5/103 33/511 |
| 5,813,132 | A * | 9/1998 | Bodkin, Sr. | G01B 5/061 33/494 |
| 5,974,678 | A * | 11/1999 | Landauer | A61B 5/107 33/512 |
| 6,003,235 | A * | 12/1999 | Chen | A61B 5/107 33/458 |
| 6,073,359 | A * | 6/2000 | Lee | A61B 5/1072 33/483 |
| 6,128,824 | A * | 10/2000 | Yang | A01K 29/00 33/464 |
| 6,178,652 | B1 * | 1/2001 | Foster | A61B 5/107 33/511 |
| 6,226,881 | B1 * | 5/2001 | Landauer | G01B 5/061 33/511 |
| 6,237,239 | B1 * | 5/2001 | Miyazaki | A61B 5/1072 33/512 |
| D455,086 | S * | 4/2002 | Chelberg | D10/70 |
| 6,401,352 | B1 * | 6/2002 | Kimura | G01B 5/061 33/703 |
| 6,446,351 | B1 * | 9/2002 | Zhang | G01B 5/061 33/556 |
| 6,557,601 | B1 * | 5/2003 | Taylor | B27B 27/02 144/253.1 |
| 6,938,355 | B1 * | 9/2005 | Duval | G01B 5/066 33/832 |
| 6,982,929 | B2 * | 1/2006 | Moss | A61B 5/1072 181/124 |
| 7,181,861 | B1 * | 2/2007 | Leser | A61B 5/1072 33/494 |
| 7,200,952 | B2 * | 4/2007 | Montagnino | A61B 5/0537 33/512 |
| 7,484,311 | B2 * | 2/2009 | Bommarito | A47G 1/205 33/613 |
| D592,535 | S * | 5/2009 | Li | D10/93 |
| 7,543,395 | B2 * | 6/2009 | Silberman | G01B 3/08 33/832 |
| D611,369 | S | 3/2010 | Garthoff | |
| 7,707,740 | B2 * | 5/2010 | Li | G01B 5/061 33/832 |
| 7,770,301 | B1 * | 8/2010 | Grandberry | G01B 3/04 33/494 |
| 7,874,971 | B2 | 1/2011 | Reyes | |
| 7,987,612 | B2 * | 8/2011 | Hong | A61B 5/1072 33/832 |
| 8,006,400 | B2 * | 8/2011 | Gerster | G01G 19/445 33/512 |
| 8,109,008 | B1 * | 2/2012 | Niemczak | A61B 5/1072 33/832 |
| 8,201,342 | B2 * | 6/2012 | Gerster | G01G 19/50 33/512 |
| D667,323 | S * | 9/2012 | Niemczak | A61B 5/1079 D10/70 |
| 8,322,043 | B2 * | 12/2012 | Cha | A61B 5/1072 33/832 |
| D678,088 | S * | 3/2013 | Haykeen | D10/70 |
| 8,425,434 | B2 * | 4/2013 | Mulder | A01K 29/00 600/587 |
| 8,528,221 | B2 * | 9/2013 | Glock, Jr. | A61B 5/1072 33/512 |
| 8,539,690 | B2 * | 9/2013 | Haykeen | A61B 5/1072 33/512 |
| D699,132 | S * | 2/2014 | Haykeen | D10/70 |
| 8,869,415 | B1 * | 10/2014 | Haykeen | A61B 5/1072 33/512 |
| 9,207,057 | B2 * | 12/2015 | Von Maydell | A61B 5/1072 |
| 9,389,056 | B2 * | 7/2016 | Wood | G01B 3/20 |
| D767,420 | S | 9/2016 | Wietzke | |
| D783,428 | S | 4/2017 | Rhein | |
| D784,171 | S * | 4/2017 | Wietzke | D10/70 |
| 9,658,333 | B1 * | 5/2017 | Jones | A61B 5/1072 |
| 2002/0046471 | A1 * | 4/2002 | Skidmore | A61B 5/107 33/511 |
| 2003/0106233 | A1 * | 6/2003 | Jordil | G01B 5/061 33/832 |
| 2004/0107593 | A1 * | 6/2004 | Rego | A41H 1/04 33/512 |
| 2004/0111909 | A1 * | 6/2004 | Pourmanafzadeh | A61B 5/1072 33/512 |
| 2005/0155246 | A1 * | 7/2005 | Montagnino | A61B 5/4869 33/832 |
| 2007/0245583 | A1 * | 10/2007 | Tindall | A01K 29/00 33/511 |
| 2007/0266579 | A1 * | 11/2007 | Briscoe | A61B 5/1071 33/503 |
| 2008/0201970 | A1 * | 8/2008 | Townsend | A47C 31/123 33/483 |
| 2010/0287786 | A1 * | 11/2010 | Biselx | G01B 5/008 33/832 |
| 2011/0072677 | A1 * | 3/2011 | Hong | A61B 5/1072 33/832 |
| 2011/0167658 | A1 * | 7/2011 | Chul | A61B 5/1072 33/512 |
| 2012/0144686 | A1 * | 6/2012 | Haykeen | A61B 5/1072 33/512 |
| 2013/0091718 | A1 * | 4/2013 | Haykeen | A61B 5/1072 33/512 |
| 2014/0202017 | A1 * | 7/2014 | Wood | G01B 3/20 33/512 |
| 2015/0176975 | A1 * | 6/2015 | Chang | G01B 11/0608 356/4.08 |
| 2016/0073931 | A1 * | 3/2016 | Ferber | A61B 5/1072 600/592 |
| 2016/0091359 | A1 * | 3/2016 | Alam | A61B 5/1072 177/1 |
| 2019/0183386 | A1 * | 6/2019 | Johnston | A61B 5/6814 |

OTHER PUBLICATIONS

Hebert-Losier, K., et al. "Raising the standards of the calf-raise test: a systematic review." Journal of Science and Medicine in Sport 12.6 (2009): 594-602.

* cited by examiner

PATIENT MEASUREMENT DEVICE AND RELATED METHODS

CROSS-REFERENCE TO RELATED APPLICATION(S)

This application claims the benefit under 35 U.S.C. § 119(e) to U.S. Provisional Application 62/529,878, filed Jul. 7, 2017 and entitled "Physical Therapy Measurement Device Rehab Ruler," which is hereby incorporated herein by reference in its entirety.

FIELD OF THE INVENTION

The various embodiments herein relate to patient measurement devices, including such devices for use by physical therapists, occupational therapists, and other healthcare providers to assess range-of-motion and other physical capabilities and limitations of an individual and take various anthropometric measurements of a subject.

BACKGROUND OF THE INVENTION

Physical therapists and other healthcare providers often use measurement tools to assess the performance of individuals' range of motion in various physical, typically joint-related movements. In the field of rehabilitation pertaining to ankle injuries, health providers will typically measure range of motion using tools such as goniometers and rulers. Additionally, providers use stadiometers to determine the height of a subject, although these tools are typically not used for physical therapy purposes pertaining to rehabilitation outcomes.

Figure 1A:
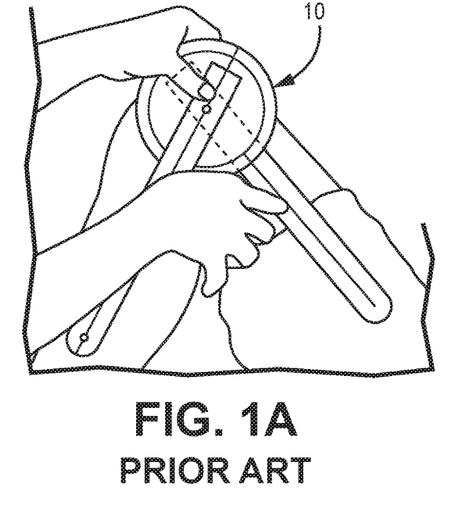
FIG. 1A depicts the use of a known goniometer to measure the range-of-motion of a patient's knee.
Figure 1B:
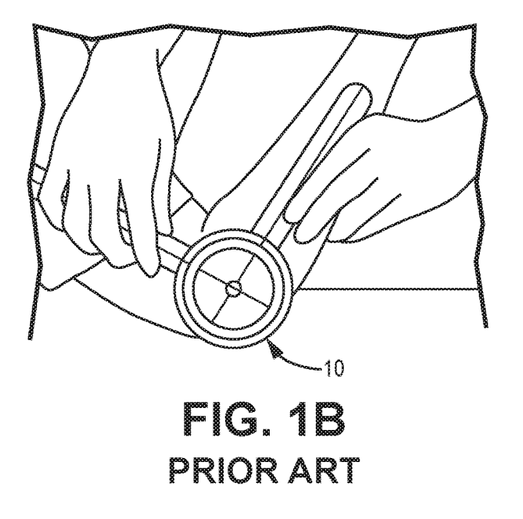
FIG. 1B depicts the use of a known goniometer to measure the range-of-motion of a patient's elbow.

Goniometers have long been used to measure joint motion over the course of rehabilitation. In these instances, as best shown in FIGS. 1A and 1B, a goniometer 10 is placed alongside the axis of a joint; the stationary arm of the goniometer 10 is aligned with a stationary body part, the moving arm of the goniometer 10 is placed alongside the moving part of the body, and movement capacity is determined by noting the change in angle between the two body parts. Rulers, likewise, have been used to measure range of motion of a subject. Both of these tools are not without limitation. One disadvantage of goniometers is significant deviation in the observed angle due to practitioner error or different methods between practitioners. Another is the lack of load bearing measurements. For example, in the case of ankle plantarflexion, the patient normally sits on a flat surface and does not place any significant amount of weight on the joint. As such, these tests fail to establish the functional range of motion of the ankle when the subject is standing and placing a load upon the joint. Similarly, traditional rulers face similar disadvantages regarding user error and device limitations.

Stadiometers have also been a staple in the medical field and are generally designed to measure a single static characteristic: patient height. As such, these devices have identical or similar designs in which a heavy stable base attaches to a vertical component, with the top of the vertical component having a sliding headpiece that rests on top of the patient's head during use. One disadvantage of stadiometers is that their current design limits their functionality and utility to practitioners in the physical rehabilitation field. That is, they are not generally used for establishing measurements pertaining to ankle plantarflexion or other anthropometric measurements that would require establishing differences in height between neutral and flexed biomechanical positions, or in measurements that would require a horizontal component.

Similar to stadiometers, the known "Sit and Reach Test" and associated equipment provides a useful but limited range-of-motion measurement. Devices used for this measurement are typically constructed as a box wherein the user's feet are placed against a side of the box, and the user reaches forward with one or both arms against a slide indicator component that moves along a series of graduations along the top of the device. One disadvantage of the "Sit and Reach" devices is that they are often limited, because they are not designed to incorporate other anthropometric tests.

There is a need in the art for an improved device and related methods for measuring range-of-motion and other anthropometric measurements in patients.

BRIEF SUMMARY OF THE INVENTION

Discussed herein are various patient measurement device implementations for taking various range-of-motion measurements, other physical capability measurements, and anthropometric measurements, and related methods.

In Example 1, a patient measurement device comprises an extendable elongate body comprising a first body comprising a lumen defined along a length of the first body, and a second body extendably disposed within the lumen of the first body, wherein the second body is axially extendable between an enclosed position and an extended position. The device further comprises a deployable arm rotatably coupled to an end of the second body, wherein the deployable arm is rotatably movable between a retracted position and a deployed position in which the deployable arm is substantially transverse to a longitudinal axis of the elongate body.

Example 2 relates to the patient measurement device according to Example 1, further comprising a coupling mechanism associated with the first body and the second body, wherein the second body is stably disposed within the lumen of the first body as a result of the coupling mechanism.

Example 3 relates to the patient measurement device according to Example 2, wherein the coupling mechanism is a friction structure coupled to the second body such that the friction structure is in frictional contact with the first body.

Example 4 relates to the patient measurement device according to Example 2, wherein the coupling mechanism is a sawtooth ratchet system.

Example 5 relates to the patient measurement device according to Example 1, wherein at least one side of the first body comprises measurement markings.

Example 6 relates to the patient measurement device according to Example 1, wherein at least one side of the second body comprises measurement markings.

Example 7 relates to the patient measurement device according to Example 1, further comprising an attachment feature disposed on a rear side of the first body.

Example 8 relates to the patient measurement device according to Example 1, wherein the attachment feature comprises adhesive.

Example 9 relates to the patient measurement device according to Example 1, further comprising a non-slip material associated with a rear side of the first body.

Example 10 relates to the patient measurement device according to Example 1, wherein the deployable arm is removably lockable in the deployed position.

In Example 11, a method of measuring range-of-motion of a particular anatomical feature of a patient comprises positioning a patient measurement device against a flat surface, the patient measurement device comprising an extendable elongate body comprising a first body comprising a lumen defined along a length of the first body, and a second body extendably disposed within the lumen of the first body, wherein the second body is axially extendable between an enclosed position and an extended position. The device further comprises a deployable arm rotatably coupled to an end of the second body, wherein the deployable arm is rotatably movable between a retracted position and a deployed position in which the deployable arm is substantially transverse to a longitudinal axis of the elongate body. The method further comprises positioning the deployable arm in the deployed position, placing a body part against the deployable arm, performing a movement that extends the body part toward the deployable arm, thereby urging the deployable arm and the second body away from the first body, and noting a length of extension of the second body out of the first body.

Example 12 relates to the method according to Example 11, wherein the flat surface comprises a vertical surface, wherein the positioning the patient measurement device further comprises positioning the patient measurement device such that the extendable elongate body is disposed substantially vertically, wherein the placing the body part against the deployable arm further comprises placing a head of the patient beneath the deployable arm, and wherein the movement comprises a single foot heel-rise.

Example 13 relates to the method according to Example 11, wherein the flat surface comprises a vertical surface, wherein the positioning the patient measurement device further comprises positioning the patient measurement device such that the extendable elongate body is disposed substantially horizontally, wherein the placing the body part against the deployable arm further comprises placing a hand of the patient against the deployable arm, and wherein the movement comprises leaning forward.

Example 14 relates to the method according to Example 13, wherein the patient performs the movement while standing.

Example 15 relates to the method according to Example 13, wherein the patient performs the movement while sitting.

Example 16 relates to the method according to Example 11, wherein the flat surface comprises a horizontal surface, wherein the positioning the patient measurement device further comprises positioning the patient measurement device between two feet of the patient such that the extendable elongate body is disposed substantially parallel to two legs of the patient, wherein the placing the body part against the deployable arm further comprises placing at least one fingertip against the deployable arm, and wherein the movement comprises leaning forward as far as physically possible while maintaining the two legs in a straight position.

In Example 17, a method of measuring range-of-motion of a particular joint of a patient comprises attaching a patient measurement device to a flat vertical surface, the patient measurement device comprising an extendable elongate body comprising a first body comprising a lumen defined along a length of the first body, and a second body extendably disposed within the lumen of the first body, wherein the second body is axially extendable between an enclosed position and an extended position. The device further comprises a deployable arm rotatably coupled to an end of the second body, wherein the deployable arm is rotatably movable between a retracted position and a deployed position in which the deployable arm is substantially transverse to a longitudinal axis of the elongate body. The method further comprises positioning the deployable arm in the deployed position, contacting the deployable arm with a body part, rotating a body joint such that the body part moves toward the deployable arm, thereby urging the deployable arm and the second body away from the first body, and noting a length of extension of the second body out of the first body.

Example 18 relates to the method according to Example 17, wherein the body part is a head of the patient, wherein the anatomical feature is an ankle joint, wherein the attaching the patient measurement device further comprises positioning the patient measurement device such that the extendable elongate body is disposed substantially vertically, wherein the length of the extension provides a measurement of a heel-rise motion.

Example 19 relates to the method according to Example 18, further comprising positioning the patient with a back against the vertical surface when contacting the deployable arm with the head of the patient.

Example 20 relates to the method according to Example 17, wherein the body part is a hand of the patient, wherein the anatomical feature is soft tissue of a posterior portion of a leg of the patient, wherein the attaching the patient measurement device further comprises positioning the patient measurement device such that the extendable elongate body is disposed substantially horizontally, wherein the length of the extension provides a measurement of reach and balance.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Each of the various patient measurement device embodiments disclosed or contemplated herein provides a portable, efficient, and health provider-friendly apparatus for measuring joint range-of-motion, positional changes, and/or other anthropometric assessments. For example, in one specific, non-limiting embodiment, the various implementations herein can measure the excursion distance of a functional heel-rise, as explained in further detail below. While many of these measurements and/or assessments are commonly performed in rehabilitation/physical therapy settings, the uses for the device and method embodiments herein are not limited thereto. In certain implementations, certain embodiments disclosed or contemplated herein can be used for multiple measurements over the course of a subject's rehabilitation period to track improvements or progress. As such, any one of these device implementations can replace goniometers, stadiometers, and "sit and reach boxes" for clinical or physical assessment purposes.

Figures 2A, 2B:
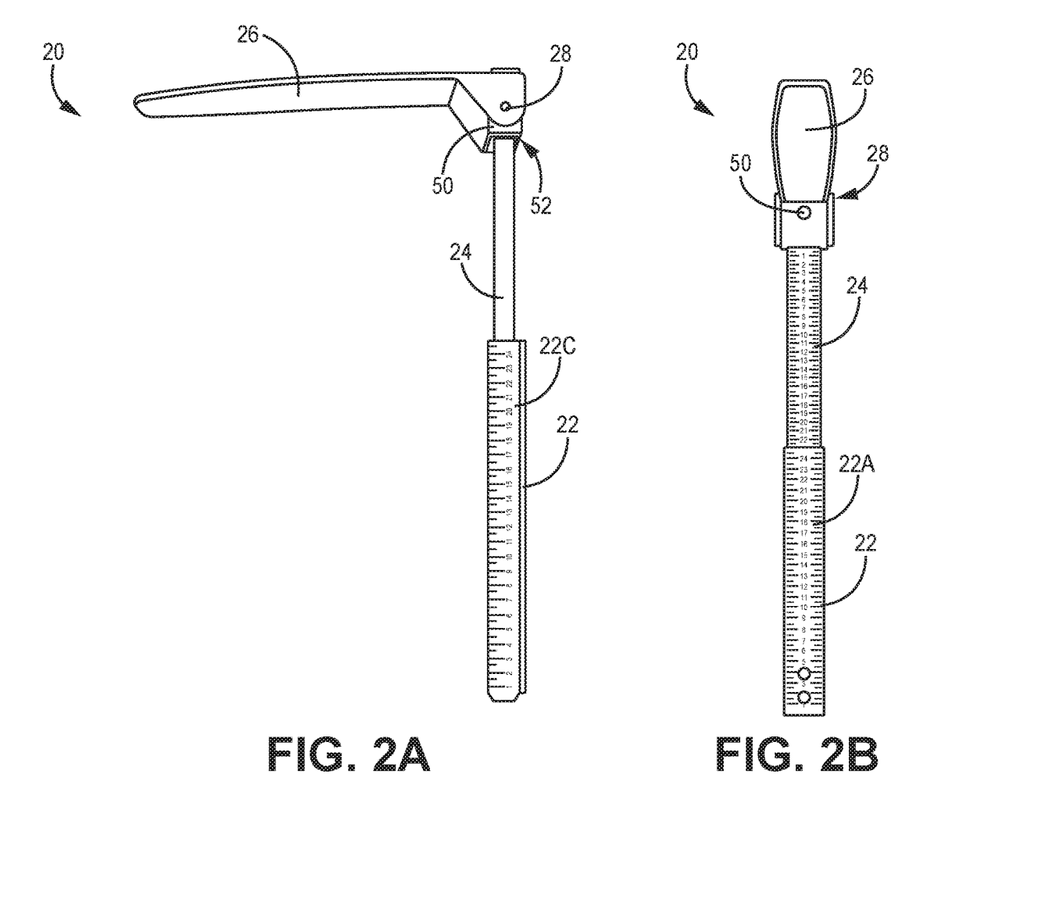
FIG. 2A is a side view of a patient measurement device with the deployable arm in the deployed position and the second body in its extended position, according to one embodiment.
FIG. 2B is a front view of the patient measurement device of FIG. 2A, according to one embodiment.
Figures 2C, 2D, 2E:
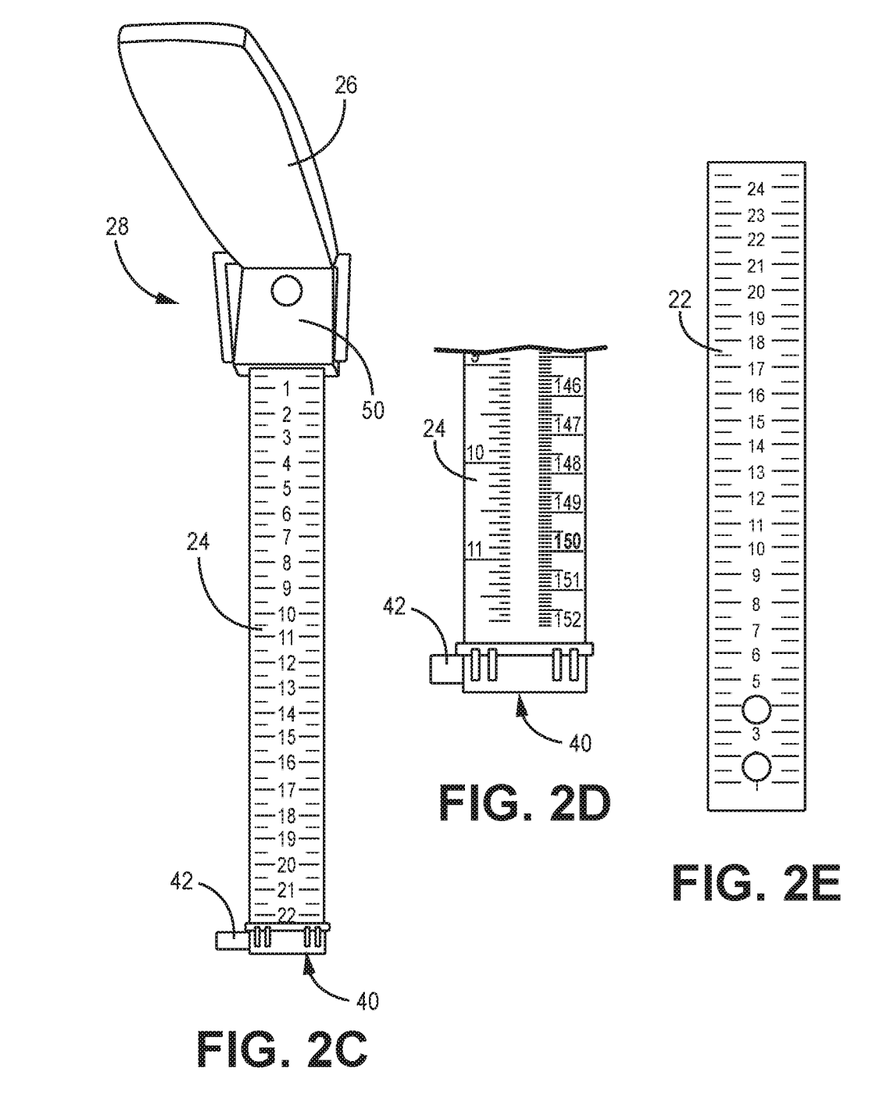
FIG. 2C is a front view of the second body and deployable arm of FIG. 2A without the first body, according to one embodiment.
FIG. 2D is a close-up front view of a portion of the second body of FIG. 2A without the first body, according to one embodiment.
FIG. 2E is a front view of the first body, according to one embodiment.
Figure 2F:
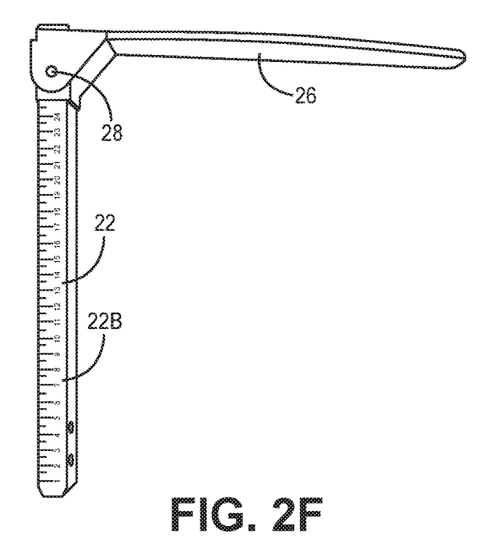
FIG. 2F is a side view of the patient measurement device of FIG. 2A with the second body in its retracted position, according to one embodiment.
Figure 2G:
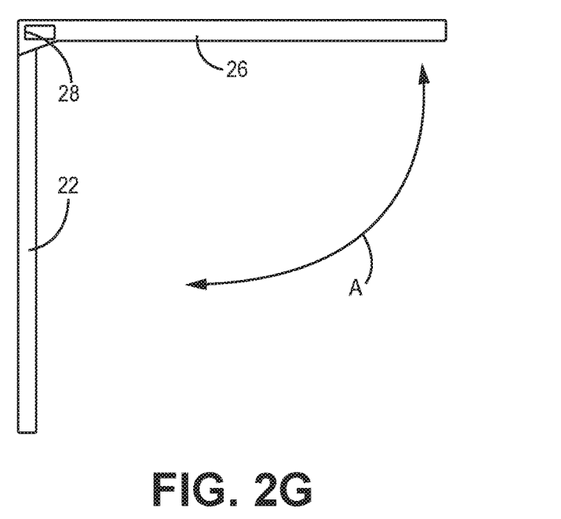
FIG. 2G is another side view of the patient measurement device of FIG. 2A with the second body in its retracted position and depicting the movement of the deployable arm, according to one embodiment.
Figure 2H:
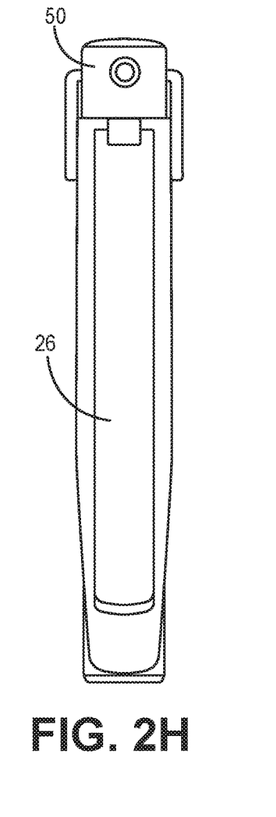
FIG. 2H is a front view of the patient measurement device of FIG. 2A with the deployable arm in the retracted position and the second body in its retracted position, according to one embodiment.
Figure 2I:
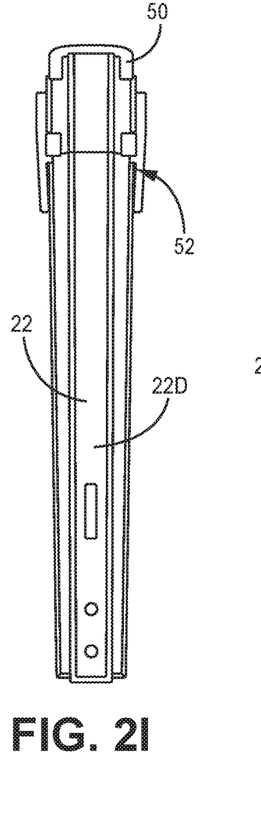
FIG. 2I is a rear view of the patient measurement device of FIG. 2H, according to one embodiment.
Figure 2J:
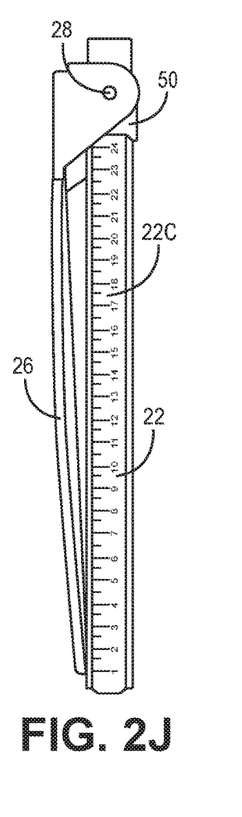
FIG. 2J is a right side view of the patient measurement device of FIG. 2H, according to one embodiment.
Figure 2K:
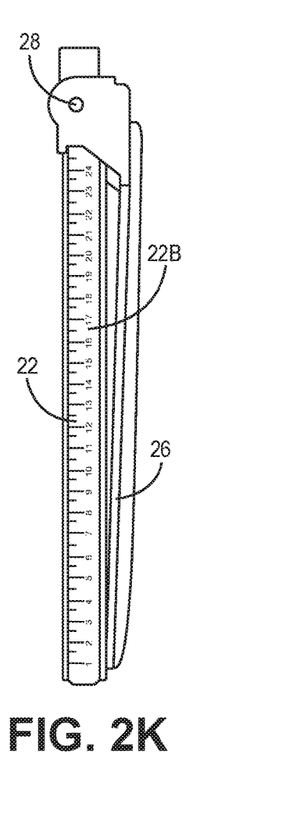
FIG. 2K is a left side view of the patient measurement device of FIG. 2H, according to one embodiment.

As best depicted in FIGS. 2A-2K, one embodiment of a measurement device 20 has a first body 22, a second body 24 that is slidable within and in relation to the first body 22, and a deployable arm 26 rotatably coupled to the second body 24 at a joint 28. The deployable arm 26, according to one implementation, is movable between a retracted position in which it is adjacent to and substantially parallel to the first and second bodies 22, 24, as best shown in FIGS. 2H, 2J, and 2K, and a deployed position in which the arm 26 extends in a transverse position in relation to the first and second bodies 22, 24, as best shown in FIGS. 2A-2C and 2F-2G. More specifically, the arm 26 can rotate around joint 28 to move as shown by arrow A in FIG. 2G between the deployed position (depicted) and the retracted position. In the deployed position, the arm 26 is generally transverse to the first and second bodies 22, 24 as shown, but it is understood that the deployed arm 26 can be disposed at a substantially transverse position. That is, the deployed arm 26 need not be disposed at a perfect right angle in relation to the bodies 22, 24. According to certain embodiments for purposes of certain measurements as will be described in additional detail below, the arm 26 is moved into the deployed position so as to be placed against a relevant body part (or the body part is placed against the arm) to measure a predetermined movement. When not in use, the arm 26 can be moved into the retracted position to reduce the size of the device 20 for portability and storage.

The second body 24 can slide axially in relation to the first body 22 such that the second body 24 can move between a retracted or non-extended position in which the second body 24 is fully or substantially disposed within the first body 22 as best shown in FIGS. 2F-2K, and a fully deployed or extended position as best shown in FIGS. 2A and 2B, or any position therebetween. The disassembled first and second bodies 22, 24 are best depicted in FIGS. 2C, 2D, and 2E. That is, FIG. 2E depicts the first body 22 and FIG. 2C depicts the second body 24 and deployable arm 26.

In certain implementations, the first body 22 can be considered a stationary body 22 such that the second body 24 is a movable body 24 that is axially slidable in relation to and within the stationary body 22. In these embodiments, the stationary body 22 can be removably attachable to a surface (such as a wall, floor, table, or any other known flat surface to which the device 20 could be attached) such that the movable body 24 can move in relation to both the stationary body 22 and the surface (not shown) to which the body 22 is attached. In certain implementations, an attachment apparatus or feature can be coupled to or otherwise associated with the rear side 22D (as described in detail below) of the stationary body 22 such that the rear side 22D of the stationary body 22 can be attached to the target surface in a fashion similar to that shown in FIGS. 3A and 3B, which will be discussed in further detail below. Exemplary attachment apparatuses/features can include, for example, adhesive, Velcro®, or any other known feature, mechanism, or component for attaching the device 20 to a flat surface for use in any of the measurements disclosed or contemplated herein.

The first body 22 is an elongate body 22 having a front side 22A (as best shown in FIG. 2B), a left side 22B (as best shown in FIGS. 2F and 2K), a right side 22C (as best shown in FIGS. 2A and 2J), and a rear side 22D (as best shown in FIG. 2I). The sides define the elongate body 22 such that the body 22 has a lumen (not shown) defined within the body 22 that is sized to slidably receive the second body 24 within the lumen as best shown in FIGS. 2A and 2B. In certain embodiments as shown in FIGS. 2A-2F and 2J-2K, at least one of the sides 22A, 22B, 22C has measurement markings such as those depicted. For example, in the specific embodiment as shown, measurement markings are provided on the front side 22A, the left side 22B, and the right side 22C, thereby making it possible to use the device 20 for various types of range-of-motion and anthropometric measurements as described in additional detail below. Alternatively, the measurement markings can be provided on any one or two of those sides (the front 22A, left 22B, and/or right 22C sides).

As described above, the second body 24 is structured to fit within the lumen of the first body 22 and slide in relation thereto. Further, as best shown in FIGS. 2C and 2D, the second body 24 has a coupling mechanism 40 that prevents entirely free movement between the second body 24 and the first body 22. In one embodiment, the coupling mechanism 40 is a friction structure 40 that maintains a frictional relationship between the second body 24 and the first body 22 when the second body 24 is disposed within the first body 22, thereby providing some resistance to the movement between the two bodies 22, 24. In other words, the coupling mechanism 40 is configured to prevent unintended, free movement of the second body 24 in relation to the first body 22. This enhanced stability of the second body 24 in relation to the first body 22 allows for the two bodies 22, 24 to remain in any predetermined position during use, thereby allowing for the health provider or other user to accurately attain the appropriate measurement readings. The friction structure 40 in this specific example is a spring-loaded mechanism 40 disposed at one end of the second body 24 that has a spring-loaded protrusion 42 that extends from friction structure 40 such that the protrusion 42 is continually urged outward from the structure 40. Thus, when the second body 24 is disposed within the lumen of the first body 22, the spring-loaded protrusion 42 is urged toward and into contact with the inner surface of the lumen of the first body 22, thereby creating friction between the two bodies 22, 24, which creates a predetermined amount of resistance to the axial movement of the second body 24 in relation to the first body 22 (or axial movement of the first 22 in relation to the second 24). Alternatively, the friction structure 40 can be disposed anywhere along the length of the second body 24 that remains disposed within the lumen of the first body 22 during use. Alternatively, the coupling mechanism 40 can be any other known mechanism, structure, or feature that provides some amount of resistance to the free movement of the two bodies 22, 24 in relation to each other. For example, the coupling mechanism 40 can be a saw tooth ratcheting component wherein the second body 24 travels along a series of teeth as it moves axially in relation to the first body 22, thereby preventing free movement between the bodies 22, 24.

In certain embodiments, the length of the first and second bodies 22, 24 are the same or similar. Alternatively, the lengths of the two bodies 22, 24 need not be similar. Instead, in certain embodiments, the second body 24 is shorter than the first body 22.

According to one implementation, the first and second bodies 22, 24 are made of any known type of metal for use in such measurement devices, such as steel, aluminum, or any other known strong, lightweight alloy. Alternatively, the bodies 22, 24 can be made of any polymeric or plastic material, such as, for example, polypropylene, polyethylene, polycarbonate, or polyvinyl chloride. In a further embodiment, the bodies 22, 24 can be made of a composite material, such as fiberglass, carbon fiber, or any other known composite material.

As described above, the deployable arm 26 is movable around the joint 28 between a retracted position and a deployed position for use in various measurements as described in detail below. In one specific embodiment as best shown in FIGS. 2A-C and 2H-K, the deployable arm 26 is rotatably coupled to a stationary attachment structure 50 that creates the joint 28. The stationary attachment structure 50 is coupled to the second body 24 such that the deployable arm 26 is rotatably attached to one end of the body 24 as shown. More specifically, the deployable arm 26 is rotatably coupled to the stationary structure 50 at the joint 28, and the stationary structure 50 is attached to the second body 24. In one embodiment, the stationary attachment structure 50 is coupled to the second body 24 via an opening 52 (as best shown in FIGS. 2A and 2I) that is defined by the stationary structure 50 and is sized and structured to receive the second body 24, as best shown in FIGS. 2I-2K, such that the structure 50 is disposed on and attached to the second body 24. Alternatively, the deployable arm 26 can be rotatably coupled to the second body 24 by any known structure, mechanism, or feature.

In certain embodiments, the deployable arm 26 is configured to be removably lockable in the deployed and retracted positions. That is, the arm 26 and stationary attachment structure 50 can have any known mechanism such that once the arm 26 is disposed in either desired position (the deployed or retracted position), a predetermined amount of additional force (beyond the force necessary to otherwise move the arm 26) is required to be applied to move the arm 26 from that position. This feature prevents free movement of the arm 26 from the deployed or retracted position while in use. In one implementation, the "locking" mechanism is a known mechanism having two inwardly (toward the stationary structure 50) extending protrusions (not shown) on the arm 26 that are parallel to the axis of the joint 28. When the deployable arm 26 is urged toward one of the deployed or retracted positions, the protrusions move around or over a chamfered and raised section on the side of the stationary structure 50 such that when the deployable arm 26 reaches the desired position (either the deployed or retracted position), the protrusions have moved past the chamfered and raised section, effectively creating the locking position where the protrusions are no longer in tension against the chamfered and raised section and such that additional force is required to urge the protrusions back over that chamfered and raised section.

In one embodiment, the deployable arm 26 and stationary structure 50 are made of a known polymeric or plastic material such as, for example, polypropylene, polystyrene, polyethylene, polycarbonate, or polyvinyl chloride. Alternatively, the deployable arm 26 can be made of steel, aluminum, or any other known strong yet lightweight alloy. In a further alternative, the arm 26 can be made of fiberglass, carbon fiber, or any other known composite material.

FIGS. 2H-2K depict the device 20 in its most compact configuration. That is, the second body 24 is disposed in its retracted position in which the second body 24 is fully or substantially disposed within the first body 22 (such that the second body 24 is not visible in those figures), and the deployable arm 26 is disposed in its retracted position. These figures reveal the ease with which the device 20 can be transported or otherwise moved by a user due to its lightweight and compact configuration, which minimizes the necessary space required to store or transport the device 20. It is understood that any dimensions and any related ratios provided or depicted herein are not limiting but instead are intended to be illustrative for the purpose of providing context to the general size of the device 20 for the purpose of general structure, features, and portability.

Figure 3A:
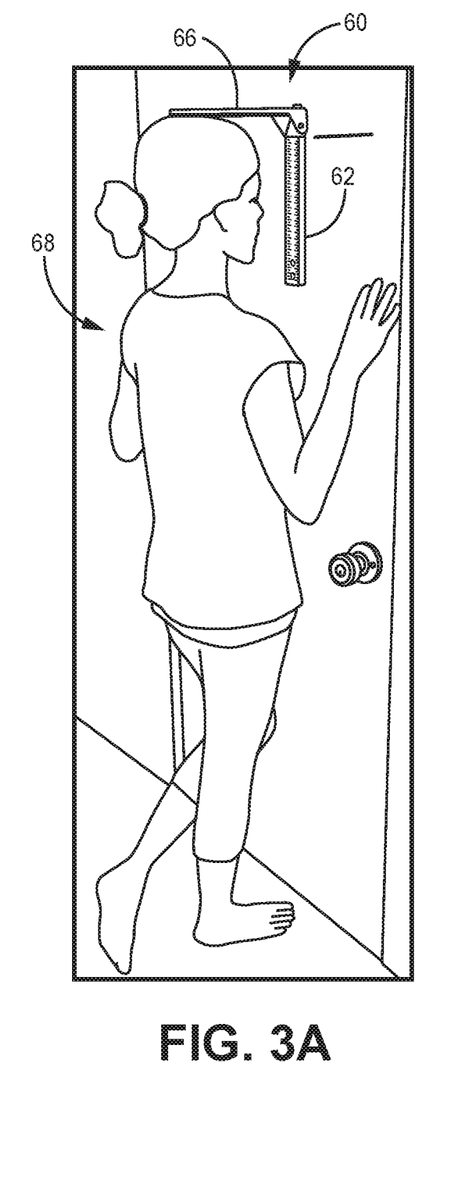
FIG. 3A depicts a patient preparing to use a patient measurement device to measure the patient's functional heel-rise in a standing position, according to one embodiment.
Figure 3B:
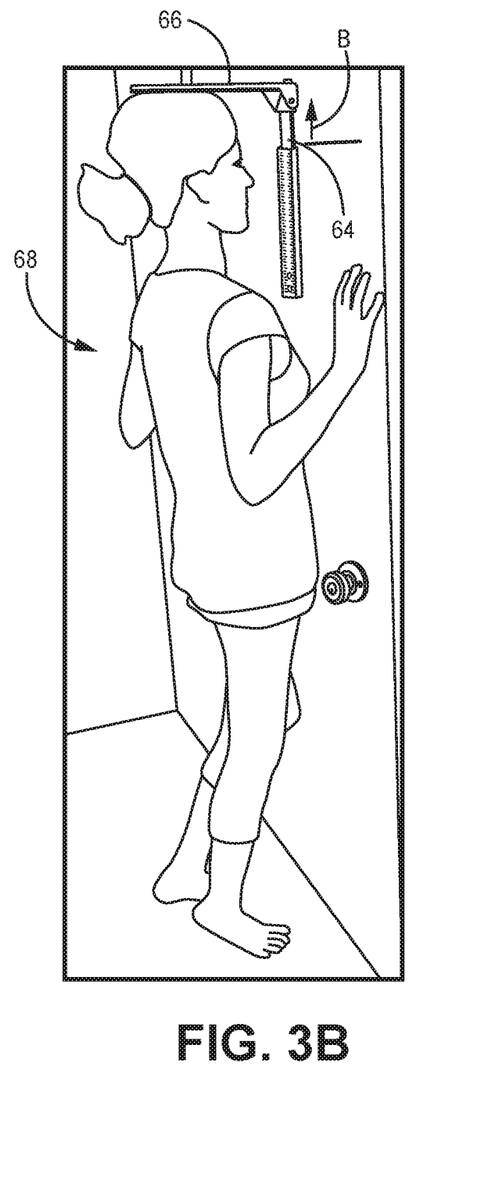
FIG. 3B depicts the patient of FIG. 3A using the patient measurement device to measure the patient's functional heel-rise in a standing position, according to one embodiment.

FIGS. 3A and 3B depict the use of a measurement device 60 according to any of the embodiments disclosed or contemplated herein by a patient 68 to measure functional heel-rise in a standing position. That is, the device 60 can be used to determine the difference between a neutral standing height of the patient 68 and height during a single ankle plantarflexion. In use, the measurement device 60 is attached to or otherwise positioned against a vertical surface (in this case, a door). More specifically, the first body 62 is attached to or positioned against the vertical surface. In certain embodiments in which the device 60 is not attached, the patient or another person can hold the device in position during the measurements as described herein. The patient 68 starts as shown in FIG. 3A in the standing position with the patient's foot flat on the floor and the patient's head in contact with the underside of the deployable arm 66. Once the patient 68 is positioned appropriately as described, the patient then performs a heel-rise by lifting her heel off of the floor and extending it upward as high as possible while maintaining her head in contact with the deployable arm 66, as shown in FIG. 3B. As such, the patient's head urges the deployable arm 66 upward as shown by arrow B in FIG. 3B by the same distance that the patient 68 raises her heel, thereby providing a measurement of the heel-rise that is measured in the distance that the deployable arm 62 and the second body 64 are urged upward into an extended position, as measured by the markings on the second body 64 in the final, extended position.

While the patient depicted in the figures herein is a female and the description discusses the various device and method embodiments in the context of that female, it is understood that the various device embodiments can be used by anyone regardless of gender identity.

According to one embodiment, this method as described above and depicted in FIGS. 3A and 3B improves upon known goniometers for the purpose of ankle-related rehabilitation by establishing a standing position with a loaded weight, which indicates the functional use of the ankle. In contrast, known goniometers used according to generally accepted techniques typically provide only a non-loaded plantarflexion measurement.

Figure 4A:
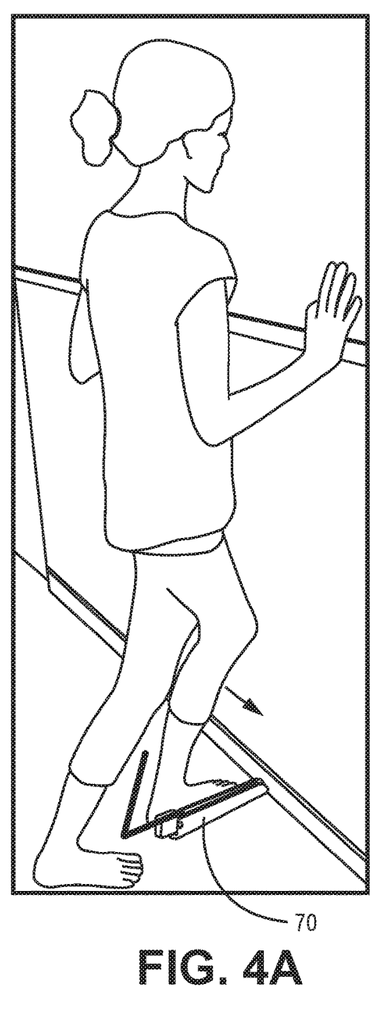
FIG. 4A depicts a patient using a patient measurement device to measure ankle dorsiflexion in a standing lunge position, according to one embodiment.
Figure 4B:
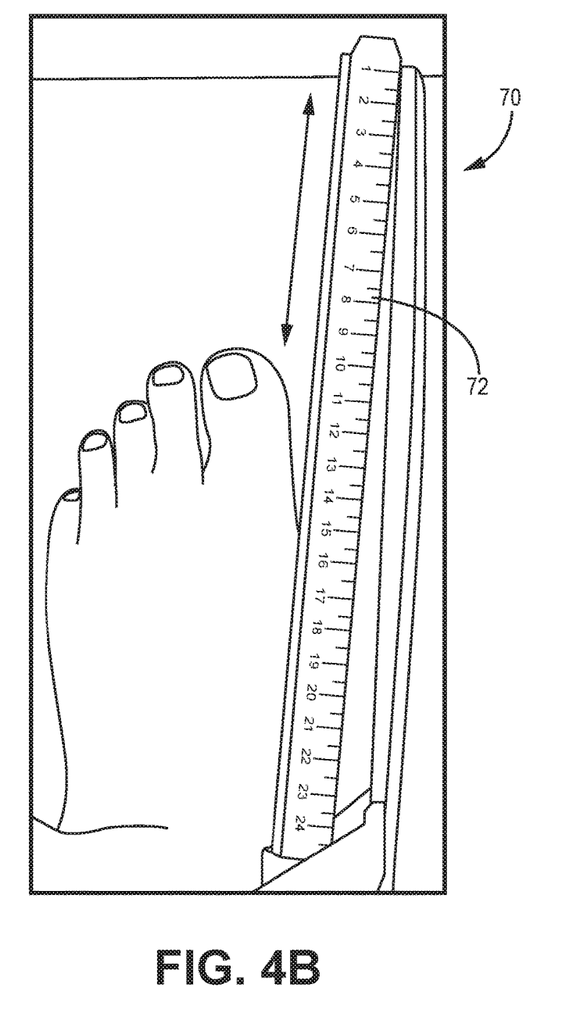
FIG. 4B depicts a close-up of the foot of the patient of FIG. 4A positioned next to the patient measurement device while measuring ankle dorsiflexion in a standing lunge position, according to one embodiment.

According to another embodiment as best shown in FIGS. 4A and 4B, a measurement device 70 according to any implementation herein can be used to measure functional, weight-bearing ankle dorsiflexion in a standing lunge position. More specifically, the device 70 is used to measure the maximal distance between the great toe and the floor-wall interface. In use, the device 70 is positioned on the floor against a vertical surface (such as, for example, a wall) as shown in the figure with the right side 72 (or left side) facing up. The patient then places her foot pointing toward the vertical surface and tilts her lower leg forward while maintaining her foot flat on the floor until the patient's knee makes contact with the wall. The patient then begins to slide or otherwise move her foot away from the wall until the patient's knee is unable to contact the wall. At this point, the distance between the patient's great toe and wall is measured for a reading of ankle dorsiflexion mobility. Similarly, this same configuration can be used to establish functional, weight-loaded pronation and supination tracking on a patient by rotating the patient 90 degrees in reference to the device 70 and performing a similar leaning posture. Further, the same technique as shown in FIGS. 4A and 4B could also be applied in the frontal plane, for ankle inversion and eversion mobility assessment.

Figure 5A:
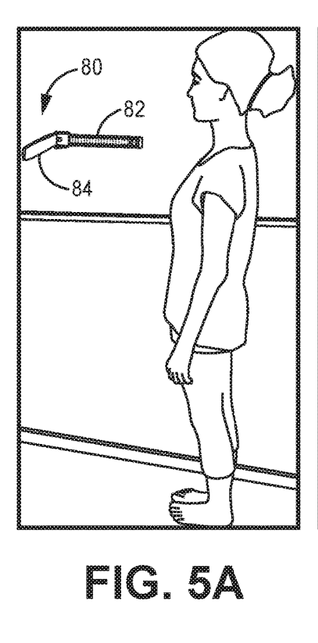
FIG. 5A depicts a patient preparing to use a patient measurement device to measure reach and balance in a standing position, according to one embodiment.
Figure 5B:
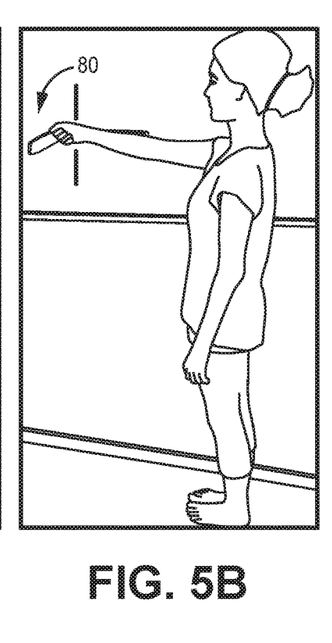
FIG. 5B depicts the patient of FIG. 5A positioning her arm in the forward flexed position in preparation for using the patient measurement device to measure reach and balance in a standing position, according to one embodiment.
Figure 5C:
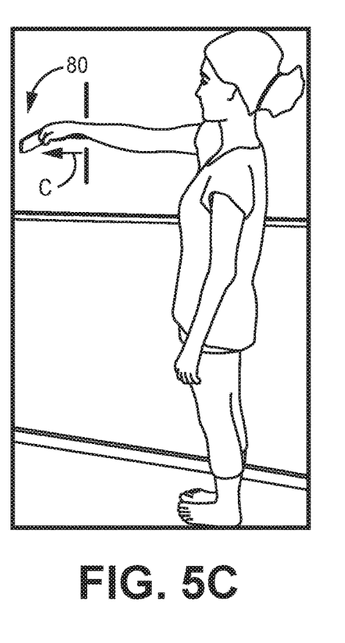
FIG. 5C depicts the patient of FIG. 5B reaching forward with her arm to measure reach and balance in the standing position using the patient measurement device, according to one embodiment.
Figure 6A:
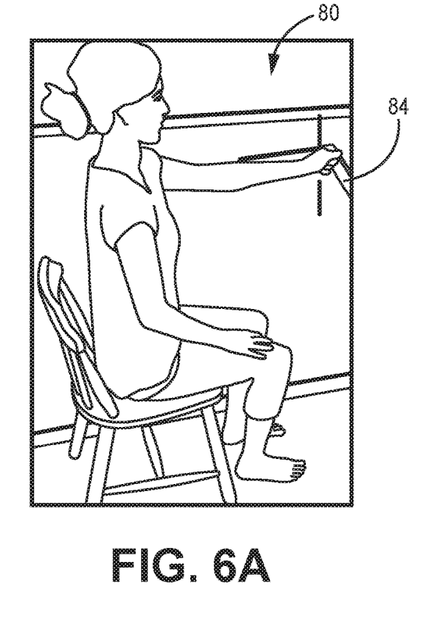
FIG. 6A depicts a patient of positioning her arm in the forward flexed position in preparation for using the patient measurement device to measure reach and balance in a sitting position, according to one embodiment.
Figure 6B:
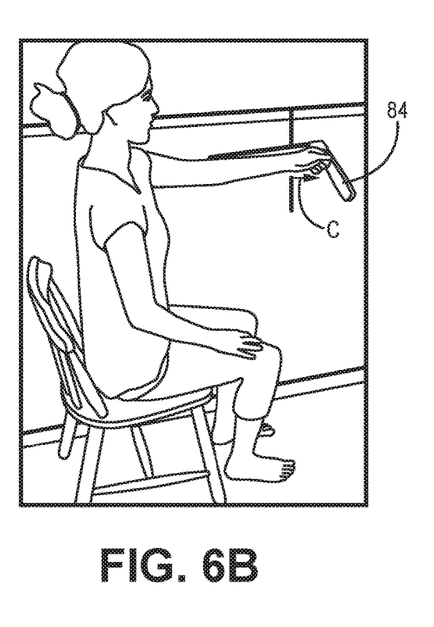
FIG. 6B depicts the patient of FIG. 6A reaching forward with her arm to measure reach and balance in the sitting position using the patient measurement device, according to one embodiment.

As shown in FIGS. 5A-6B, a device 80 can be used to assess a patient's functional reach and balance in either a standing or sitting position, according to one implementation. More specifically, FIGS. 5A-5C depict the measurement with the device 80 positioned on the wall while the patient is in a standing position, while FIGS. 6A-6B depict the measurement with the device 80 positioned lower on the wall while the patient is in the sitting position. In both measurement positions, the device 80 is positioned on the wall such that the longitudinal axis of the first body 82 is parallel to the floor (or horizontal plane), the second body (not shown) is in the fully retracted position, and the deployable arm 84 is placed in the deployed position. In either the standing or sitting position, the patient's arm is situated in the forward flexed position, as shown in FIGS. 5B and 6A, and the device 80 is attached horizontally on a vertical surface (in this specific example, a wall). In the forward flexed position, the patient's arm is extended outward away from the patient's body such that the arm is parallel to the floor (or horizontal plane) with the patient's hand clinched as shown and positioned in contact with the deployable arm 84. Then, as depicted in FIGS. 5C and 6B, and as understood by those skilled in the art, the patient then reaches forward by shifting her bodyweight and leaning in the forward direction, thereby urging the deployable arm 84 and second body (not shown) away from the patient, which causes the second body (not shown) to extend some distance out of the first body 82. The distance that the second body (not shown) extends from the first body 82 as depicted by arrow C is then measured to determine the difference between the initial reading and the final reading. Alternatively, the device 80 can be attached to a flat vertical surface (such as a wall or other stable object) at a location closer to ground level (in comparison to the locations as shown in FIGS. 5A-6B) to be used as an alternative for a "sit and reach box" as described in further detail below.

Figure 7A:
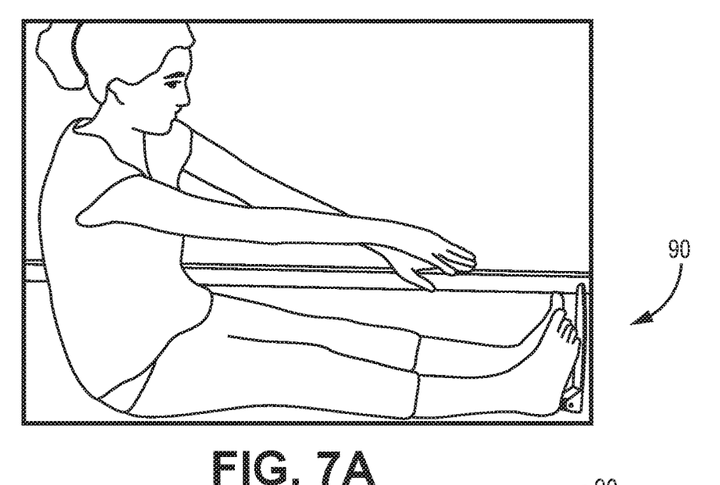
FIG. 7A depicts a patient preparing to use a patient measurement device to perform a "sit and reach test," according to one embodiment.
Figure 7B:
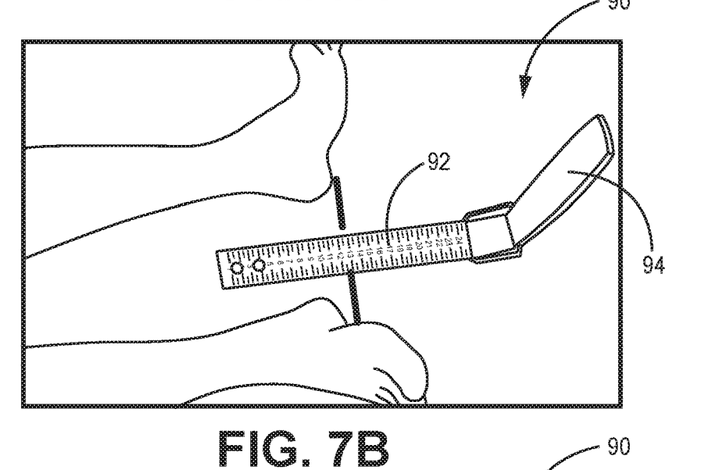
FIG. 7B depicts a close-up of the feet of the patient of FIG. 7A with the patient measurement device positioned therebetween while preparing to perform the "sit and reach test," according to one embodiment.
Figure 7C:
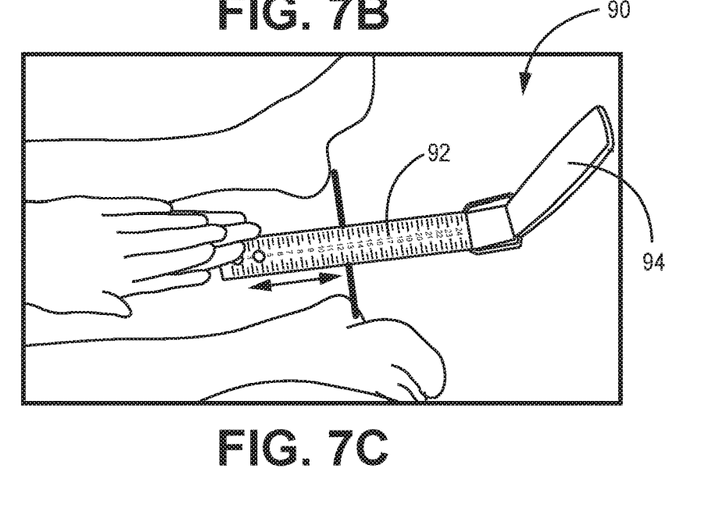
FIG. 7C depicts a close-up of the feet of the patient of FIG. 7B with the patient measurement device positioned therebetween while performing the "sit and reach test," according to one embodiment.

FIGS. 7A-7C depict a method of using a device 90 in accordance with a further embodiment to determine a patient's lower back and hamstring flexibility via a "sit and reach test," with no vertical attachment of the device 90 necessary. In this implementation, the patient positions herself on the floor with both legs extended as shown and situates the device 90 between the patient's feet at a location where the neutral and extended positions fall within the available range of graduations listed along the length of the device 90. In this specific example, the device 90 is positioned between the patient's feet and parallel to the patient's legs with the first body 92 disposed with the front side facing upward and the deployable arm 94 in the deployed position (so that the front side of the first body 92 and the markings thereon are visible). The patient then extends her arms into a neutral (non-extended) position as shown in FIG. 7A, and that measurement is taken by identifying the measurement marking on the front side to which the tip of the patient's fingers is closest. Subsequently, the patient leans forward as far as possible while keeping her legs straight (not bending the patient's knees) and that measurement is taken by identifying the measurement marking on the front side to which the tip of the patient's fingers is closest.

Continuing with FIGS. 7A-7C, in an alternative implementation, the patient is positioned on the floor with both legs extended as shown and the device 90 is positioned in the same position as described above: between the patient's feet and parallel to the patient's legs with the first body 92 disposed with the front side facing upward and the deployable arm 94 in the deployed position (so that the front side of the first body 92 and the markings thereon are visible). In contrast, in this alternative embodiment, the device 90 is positioned at a location where the deployable arm 94 is disposed at the tips of the patient's fingers when the patient has her arms outstretched in the neutral (non-extended) position before the test begins as best shown in FIG. 7A. For the assessment, the patient leans forward as far as possible while her arms remain outstretched, thereby pushing forward (away from the patient) the deployable arm 94 so that the second body (not shown) extends from inside of the first body 92 while keeping her legs straight (not bending the patient's knees) and a measurement may be taken based on the measurement markings on the second body.

Figure 8:
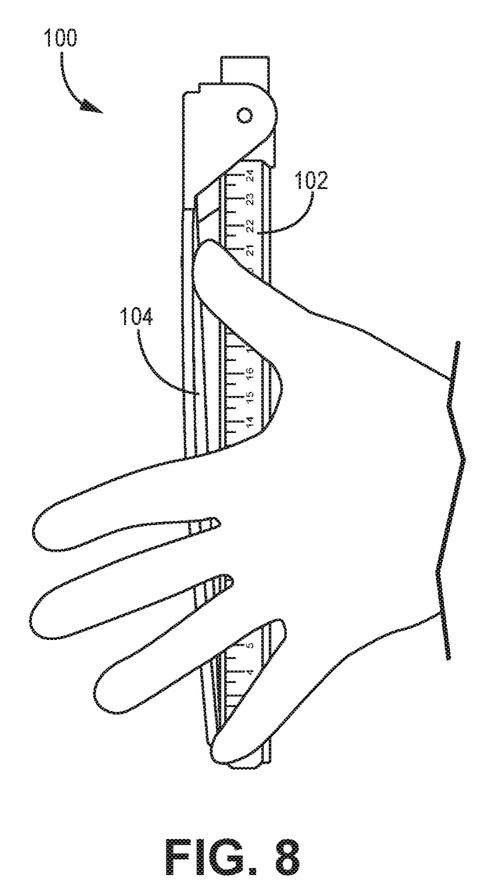
FIG. 8 depicts a hand of a patient positioned adjacent to a right side of a patient measurement device to collect anthropometric measurements of the hand, according to one embodiment.

As shown in FIG. 8 according to one embodiment, a device 100 can be used to collect various standard anthropometric measurements. For example, the device 100 can be used to measure foot length, distances relative to an anatomical landmark (such as the distance relative to the styloid process of the radius, etc.), and, as depicted in the specific example of FIG. 8, hand width (which is a measure of the maximal open position of a patient's hand). It is understood that any such anatomical and/or anthropometric measurements can be measured using the device 100. In this specific exemplary embodiment, the device 100 is disposed such that the right side of the first body 102 is positioned upward and the deployable arm 104 is positioned in its retracted position. It is understood that the device 100 can be positioned in any way with respect to the floor and in any configuration that will assist with a particular measurement.

Figure 9:
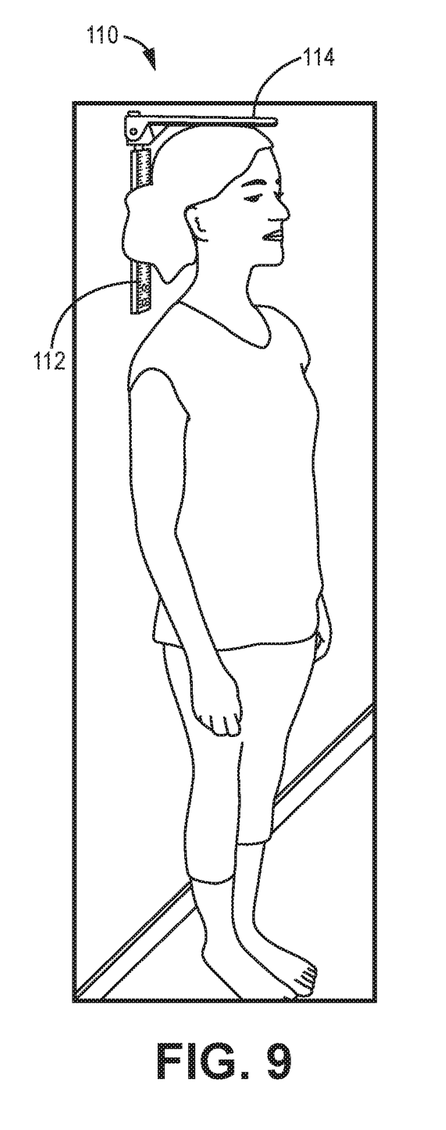
FIG. 9 depicts a patient using a patient measurement device as a height measurement device, according to one embodiment.

In accordance with another embodiment as shown in FIG. 9, a device 110 can be used as a travel-sized height measurement device 110, in place of a stadiometer. In various implementations, the device 110 can be positioned such that the first body 112 is attached to or positioned against a vertical surface (such as a wall) and used with the deployable arm 114 in its deployed position. In use, the patient stands adjacent to the wall with her back against the wall such that the patient's head is disposed under the deployable arm 114 in its deployed position. The extent to which the patient's head causes the deployable arm 114 to move upward, thereby causing the second body (not shown) to extend out of the first body 112 creates the height measurement. That is, the distance which the second body (not shown) extends out of the first body 112 as a result of the patient standing beneath the deployable arm 114 is the measurement of note, which is added to the distance between the top of the first body 112 and the floor to calculate the patient's height. To maximize accuracy of this method, according to one embodiment, a retractable tape measure may be affixed to the bottom of the first body 112 and used to precisely determine the desired mounting height of the device 110 on the vertical surface.

The foregoing description and drawings comprise illustrative embodiments of the various inventions. The foregoing embodiments and the methods described herein may vary based on the ability, experience, and preference of those skilled in the art. Merely listing certain specific uses does not constitute any limitation on other possible clinical, rehabilitative, or measuring uses. The foregoing description and drawings merely explain and illustrate the various embodiments, and they are not limited thereto, except insofar as the claims are so limited. Those skilled in the art who have the disclosure before them will be able to make modifications and variations therein without departing from the scope thereof. In other words, although various embodiments have been described herein, persons skilled in the art will recognize that changes may be made in form and detail without departing from the spirit and scope thereof.

What is claimed is:

1. A patient measurement device comprising
  (a) an extendable elongate body comprising:
    (i) a first body comprising a lumen defined along a length of the first body; and
    (ii) a second body extendably disposed within the lumen of the first body, wherein the second body is axially extendable between an enclosed position and an extended position; and
  (b) a deployable arm rotatably coupled to a stationary attachment structure that is coupled to an end of the second body, wherein the deployable arm is rotatably movable between a retracted position and a deployed position in which the deployable arm is substantially transverse to a longitudinal axis of the elongate body,
  wherein the first body extends from a first terminal end to a second terminal end along the longitudinal axis of the elongate body,
  wherein the stationary attachment structure contacts the first terminal end of the first body when the second body is in the enclosed position, and
  wherein the deployable arm includes a second end opposite a first end of the deployable arm coupled to the stationary attachment structure, the second end of the deployable arm being adjacent the second terminal end of the first body when the second body is in the enclosed position,
  wherein the second end of the deployable arm contacts the first body when the second body is in the retracted position.

2. The patient measurement device of claim 1, further comprising a coupling mechanism associated with the first body and the second body, wherein the second body is stably disposed within the lumen of the first body as a result of the coupling mechanism.

3. The patient measurement device of claim 2, wherein the coupling mechanism is a friction structure coupled to the second body such that the friction structure is in frictional contact with the first body.

4. The patient measurement device of claim 2, wherein the coupling mechanism is a sawtooth ratchet system.

5. The patient measurement device of claim 1, wherein at least one side of the first body comprises measurement markings.

6. The patient measurement device of claim 1, wherein at least one side of the second body comprises measurement markings.

7. The patient measurement device of claim 1, further comprising an attachment feature disposed on a rear side of the first body.

8. The patient measurement device of claim 7, wherein the attachment feature comprises adhesive.

9. The patient measurement device of claim 1, further comprising a non-slip material associated with a rear side of the first body.

10. The patient measurement device of claim 1, wherein the deployable arm is removably lockable in the deployed position.

11. The patient measurement device of claim 1, wherein the second body is substantially disposed within the first body when the second body is in the enclosed position.

12. The patient measurement device of claim 2, wherein the coupling mechanism comprises a spring-loaded mechanism disposed on the second body.

13. The patient measurement device of claim 12, wherein the spring-loaded mechanism comprises a spring-loaded protrusion that is urged toward and into contact with an inner surface of the lumen of the first body.

14. The patient measurement device of claim 1 wherein:
a side of the first body comprises measurement markings,
a side of the second body comprises measurement markings, and
the side of the first body and the side of the second body face in the same direction.

15. A patient measurement device comprising
(a) an extendable elongate body comprising:
(i) a first body comprising a lumen defined along a length of the first body; and
(ii) a second body extendably disposed within the lumen of the first body, wherein the second body is axially extendable between an enclosed position and an extended position; and
(b) a deployable arm rotatably coupled to a stationary attachment structure that is coupled to an end of the second body, wherein the deployable arm is rotatably movable between a retracted position and a deployed position in which the deployable arm is substantially transverse to a longitudinal axis of the elongate body,
wherein the first body extends from a first terminal end to a second terminal end along the longitudinal axis of the elongate body,
wherein the stationary attachment structure contacts the first terminal end of the first body when the second body is in the enclosed position, and wherein the deployable arm includes a second end opposite a first end of the deployable arm coupled to the stationary attachment structure, the second end of the deployable arm being adjacent the second terminal end of the first body when the second body is in the enclosed position,
wherein the first body is an outermost body of the extendable elongate body.

16. The patient measurement device of claim 15, further comprising a coupling mechanism associated with the first body and the second body, wherein the second body is stably disposed within the lumen of the first body as a result of the coupling mechanism.

17. The patient measurement device of claim 16, wherein the coupling mechanism is a friction structure coupled to the second body such that the friction structure is in frictional contact with the first body.

18. The patient measurement device of claim 16, wherein the coupling mechanism is a sawtooth ratchet system.

19. The patient measurement device of claim 15, wherein at least one side of the first body comprises measurement markings.

20. The patient measurement device of claim 15, wherein at least one side of the second body comprises measurement markings.

* * * * *